United States Patent
Linde et al.

(10) Patent No.: US 11,904,008 B2
(45) Date of Patent: Feb. 20, 2024

(54) PREPARATION OF LIVE VACCINES

(71) Applicant: Elanco Tiergesundheit AG, Greenfield, IN (US)

(72) Inventors: Klaus Linde, Cuxhaven (DE); Anke Grosse-Herrenthey, Cuxhaven (DE)

(73) Assignee: Elanco Tiergesundheit AG, Basel (CH)

( * ) Notice: Subject to any disclaimer, the term of this patent is extended or adjusted under 35 U.S.C. 154(b) by 0 days.

(21) Appl. No.: 16/985,458

(22) Filed: Aug. 5, 2020

(65) Prior Publication Data
US 2022/0088168 A1 Mar. 24, 2022

Related U.S. Application Data

(62) Division of application No. 14/440,942, filed as application No. PCT/EP2013/068373 on Sep. 5, 2013, now Pat. No. 10,828,362.

(30) Foreign Application Priority Data

Dec. 7, 2012 (EP) .................................... 12008206

(51) Int. Cl.
| | | |
|---|---|---|
| A61K 39/02 | (2006.01) | |
| A61K 39/112 | (2006.01) | |
| A61K 39/106 | (2006.01) | |
| A61K 39/00 | (2006.01) | |
| C12N 1/36 | (2006.01) | |

(52) U.S. Cl.
CPC ........ *A61K 39/105* (2013.01); *A61K 39/0275* (2013.01); *C12N 1/36* (2013.01); *A61K 2039/106* (2013.01); *A61K 2039/522* (2013.01); *A61K 2039/542* (2013.01); *A61K 2039/55* (2013.01); *A61K 2039/552* (2013.01); *Y02A 50/30* (2018.01)

(58) Field of Classification Search
None
See application file for complete search history.

(56) References Cited

U.S. PATENT DOCUMENTS

| | | |
|---|---|---|
| 5,112,749 A | 5/1992 | Brey, III et al. |
| 6,136,325 A | 10/2000 | Linde et al. |
| 6,479,056 B1 | 11/2002 | Linde et al. |
| 10,828,362 B2 * | 11/2020 | Linde .................... C12N 1/205 |

FOREIGN PATENT DOCUMENTS

| | | |
|---|---|---|
| CA | 2133401 A1 | 4/1995 |
| DE | 294420 | 10/1983 |
| DE | 294420 A5 | 10/1991 |
| DE | 102007012824 A1 | 9/2008 |
| DE | 102008062941 | 7/2010 |
| DE | 102008062941 A1 | 7/2010 |
| EP | 0263528 A2 | 4/1988 |
| EP | 0642796 A1 | 3/1995 |
| WO | 199507101 | 3/1995 |
| WO | 1999049026 | 9/1999 |
| WO | 2004089408 | 10/2004 |
| WO | 2005078068 | 8/2005 |

OTHER PUBLICATIONS

Weyer H. et al. Arch. Exp. Veterinarmed. 1973; 27(2): 301-320.
Linde K. et al. Acta Microbiol. Acad. Sci. Hung. 1974; 21(1-2): 11-27.
Schimmel D. et al "The use of a streptomycin-dependent mutant of *Salmonella typhimurium* in chickens", Arch. Exp. Veterinarmed. 1974; 28(4): 551-558.
Meyer H. et al. Arch Exp Veterinarmed. 1977; 31(1): 71-93.
Meyer H. et al. Arch Exp Veterinarmed. 1977; 31(1): 95-113.
Meyer H. et al. Arch Exp Veterinarmed. 1977; 31(2): 277-288.
Linde K. and Keller, H.P. Zschr. F. ges. Hyg. and Grenzgebiete 1978, 24, 6, 452-458.
Linde K. Arch Exp Veterinarmed. 1980; 34(1): 19-32.
Linde K., Zbl. Bakt. Hyg. I. Abt. 1981, 249, 350-361.
Linde K. Zentralbl Bakteriol A. 1981; 249(2): 203-214.
Linde K. and Mitarb. Zbl. Bakt. Hyg. I Abt. Orig. A 1981, 250, 478-489.
Linde K. Arch. Exper. Vet. Med. 1982, 36, 647-656.
Linde K. Dev. Biol. Standard 1983, 53, 15-28.
Linde K. et al. Arch. Exper. Vet. Med. 1983, 37, 353-360.
Linde K. et al. Z Gesamte Hyg. Mar. 30, 1984(3): 141-147.
Polotskii Iue, B. et al. "The morphological assessment of the safety and protective activity of the vaccinal strain *Salmonella typhimurium* 274", Zh Mikrobiol Epidemiol Immunobiol. Apr. 1992; (4): 33-37.
Filho, "Control of *Salmonella enteritidis* and *Salmonella gallinarum* in birds by using live vaccine candidate containing attenuated *Salmonella gallinarum* mutant strain", Vaccine, 2010, pp. 2853-2859, vol. 28.
Linde, "Stable *Salmonella* live vaccine strains with two or more attenuating mutations and any desired level of attenuation", Vaccine, 1990, pp. 278-282, vol. 8.
Shehata, "Safety and Efficacy of a Metabolic Drift Live Attenuated *Salmonella gallinarum* Vaccine Against Fowl Typhoid", Avian Disease, 2013, pp. 29-35, vol. 57.
Goldschmidt et al. Genetic Analyses of Mutations from Streptomycin Dependence to Independence in Salmonella Typhimurium. Genetics. Nov. 1962; 47(11): 1475-1487.
International Search Report and Written Opinion for PCT/EP2013/068373 dated Oct. 22, 2013. pp. 1-12.
European Search Report for Application EP12008206 completed Apr. 16, 2013. pp. 1-8.
European Search Report for Application EP18181260 completed Nov. 13, 2018. pp. 1-11.
European Search Report for Application EP20157537 completed Aug. 13, 2020. pp. 1-12.

(Continued)

*Primary Examiner* — S. Devi
(74) *Attorney, Agent, or Firm* — Barnes & Thornburg LLP

(57) ABSTRACT

Described is a method for the generation of a live vaccine containing stable bacteria carrying at least three attenuating mutations and a vaccine containing bacteria obtained by said method.

11 Claims, 6 Drawing Sheets

(56) References Cited

OTHER PUBLICATIONS

Figure 1A:
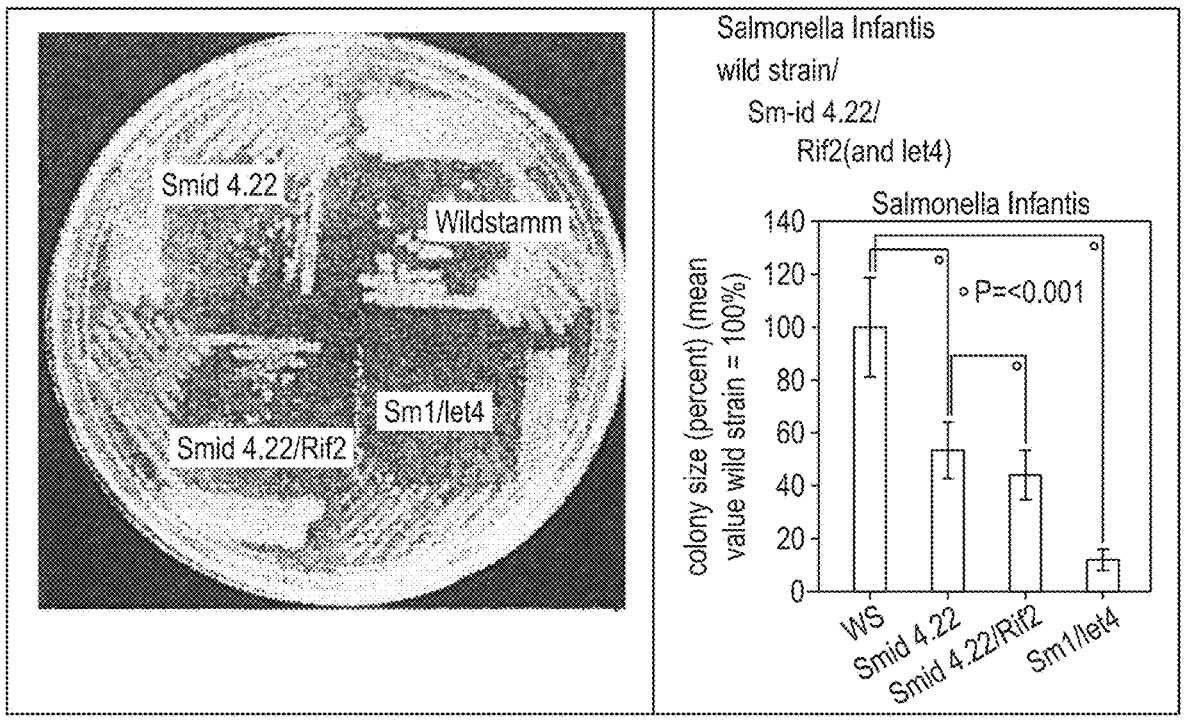
Figure 1B:
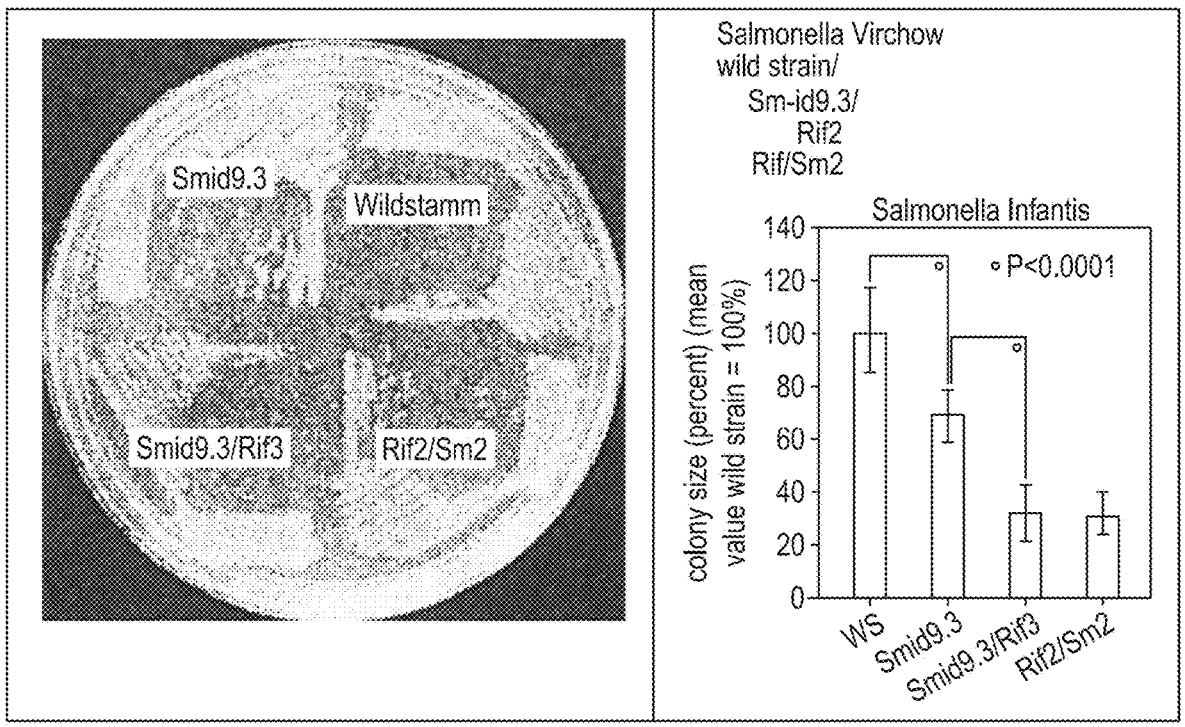
Figure 1C:
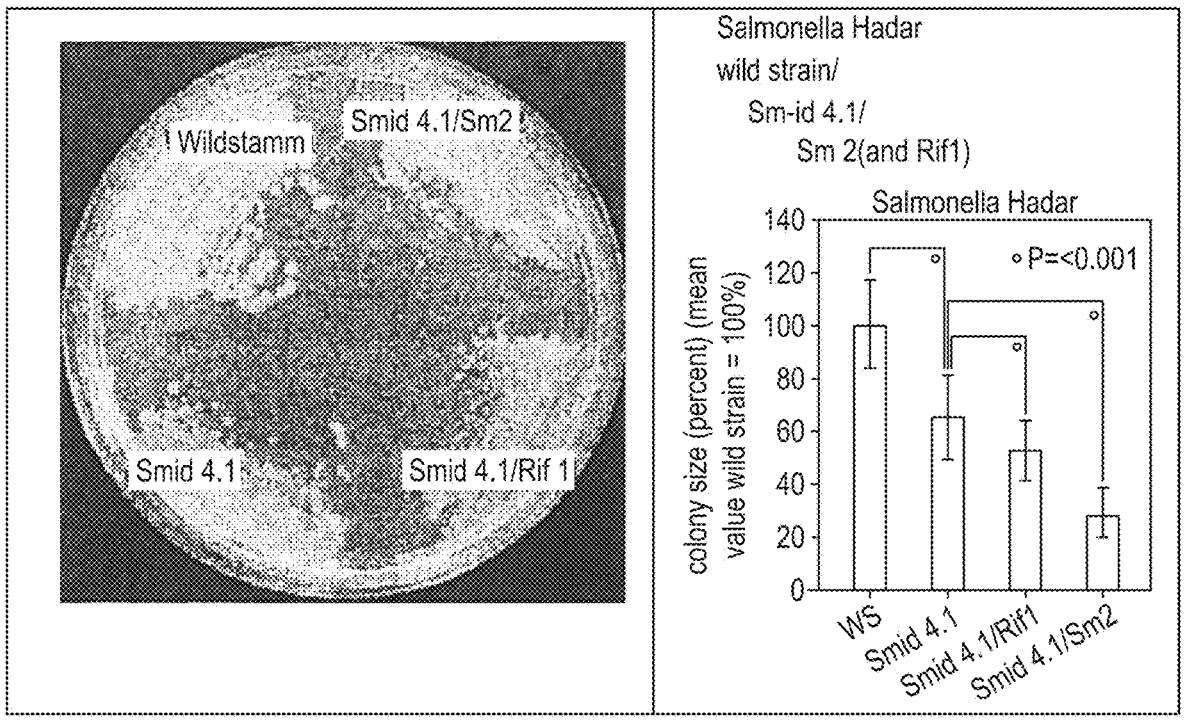
Figure 1D:
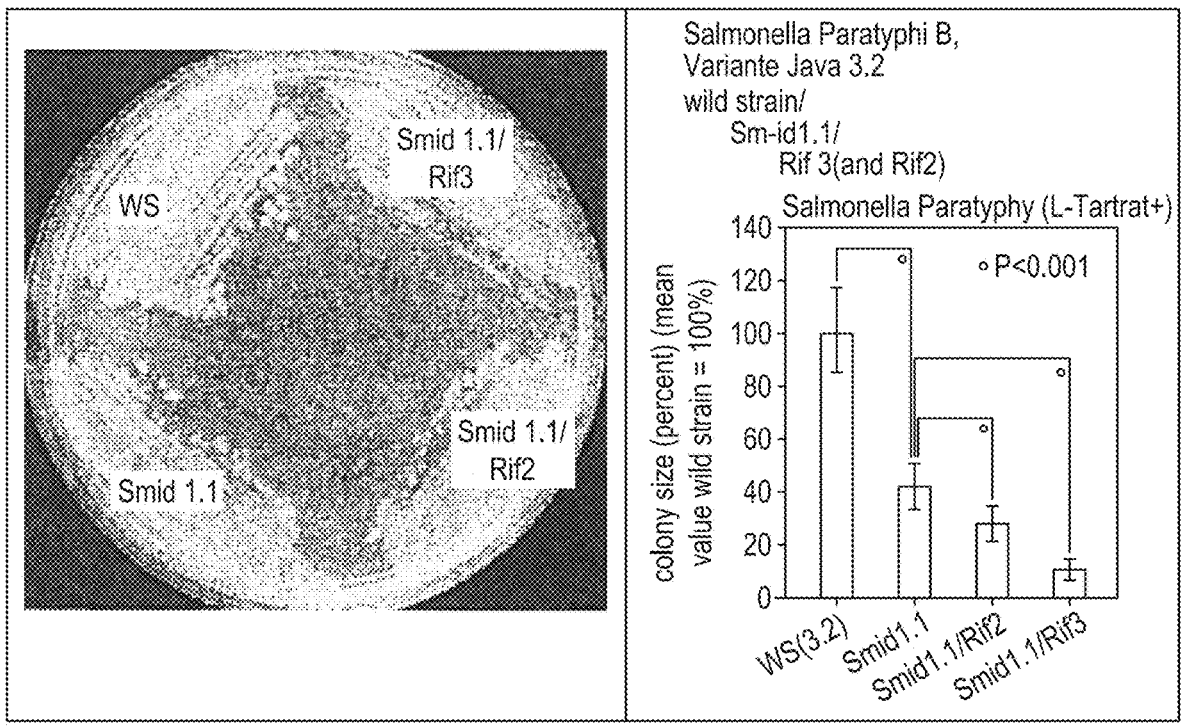
Figure 2A:
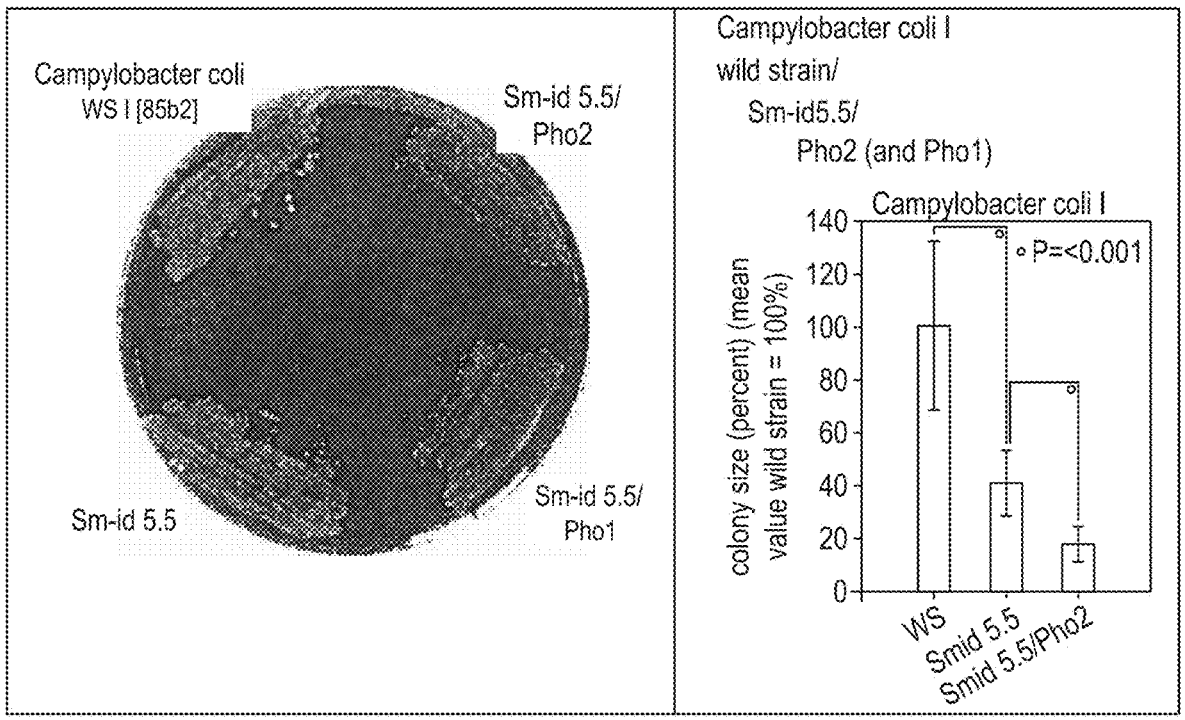
Figure 2B:
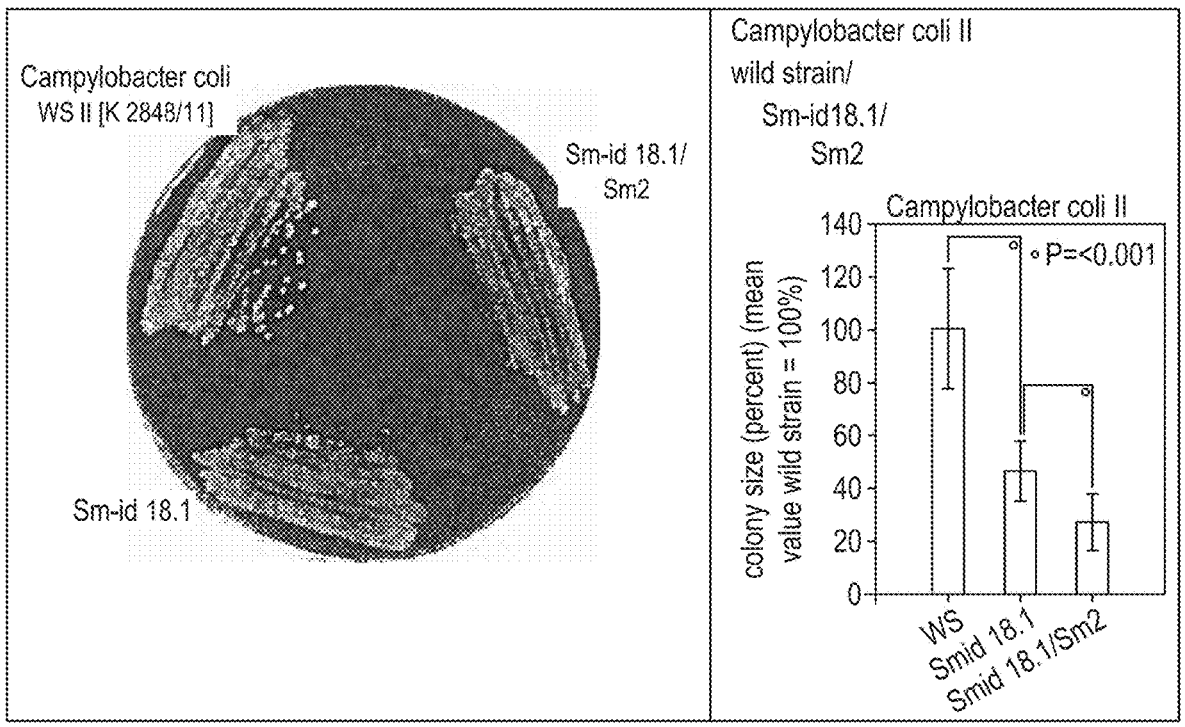
Figure 2C:
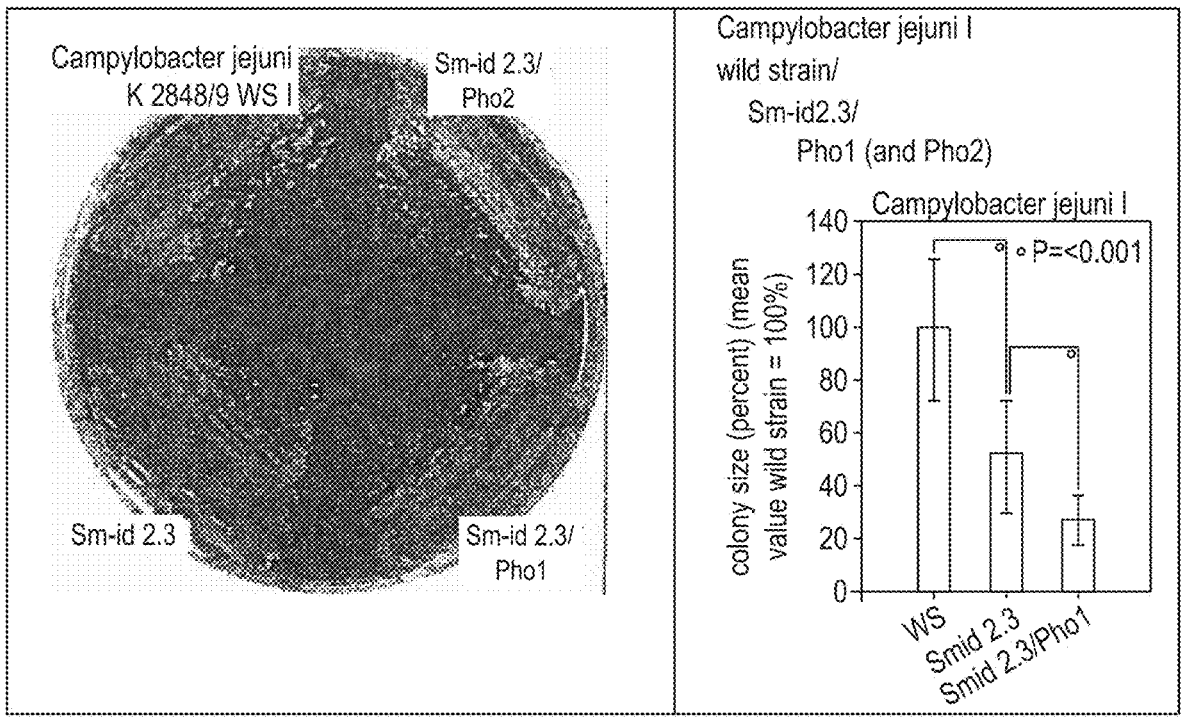
Figure 2D:
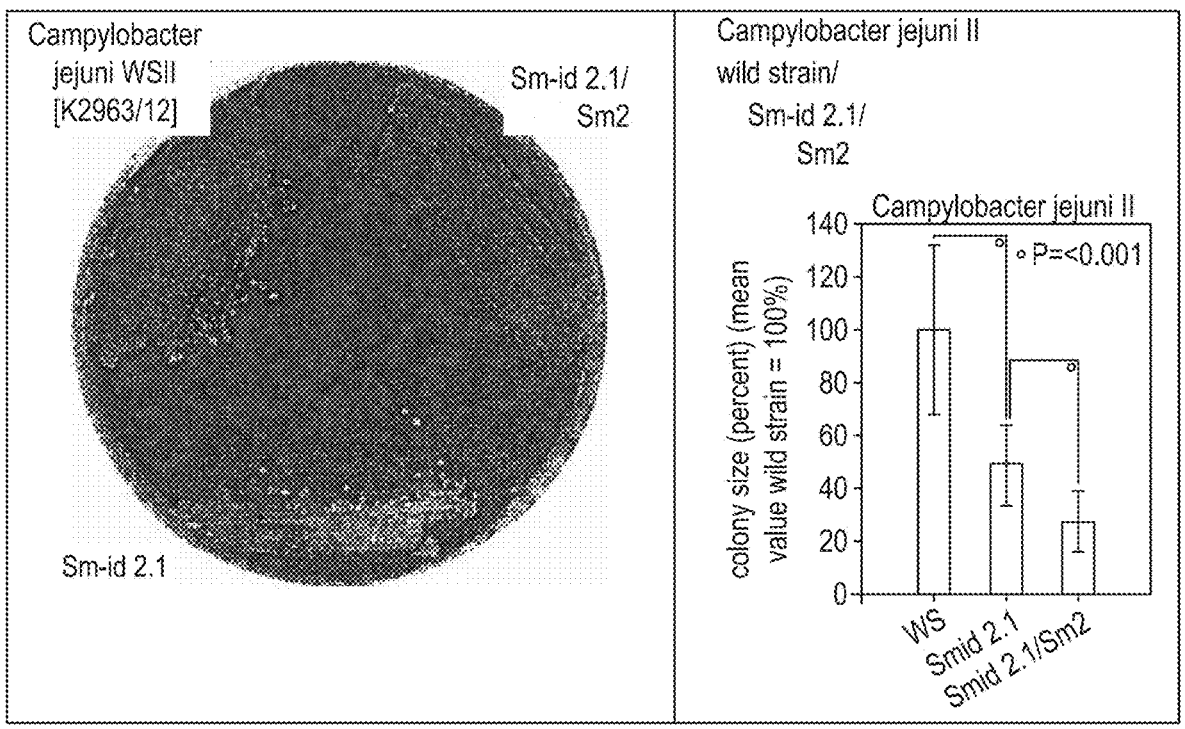
Figure 3A:
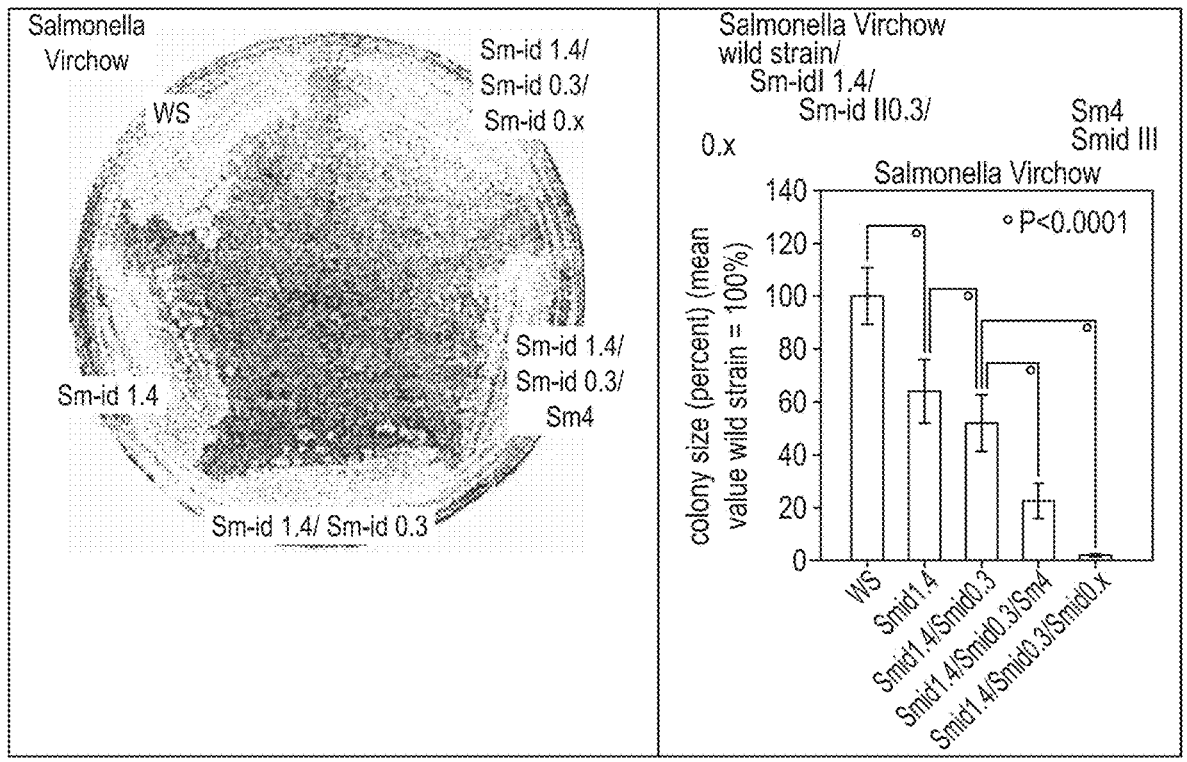
Figure 3B:
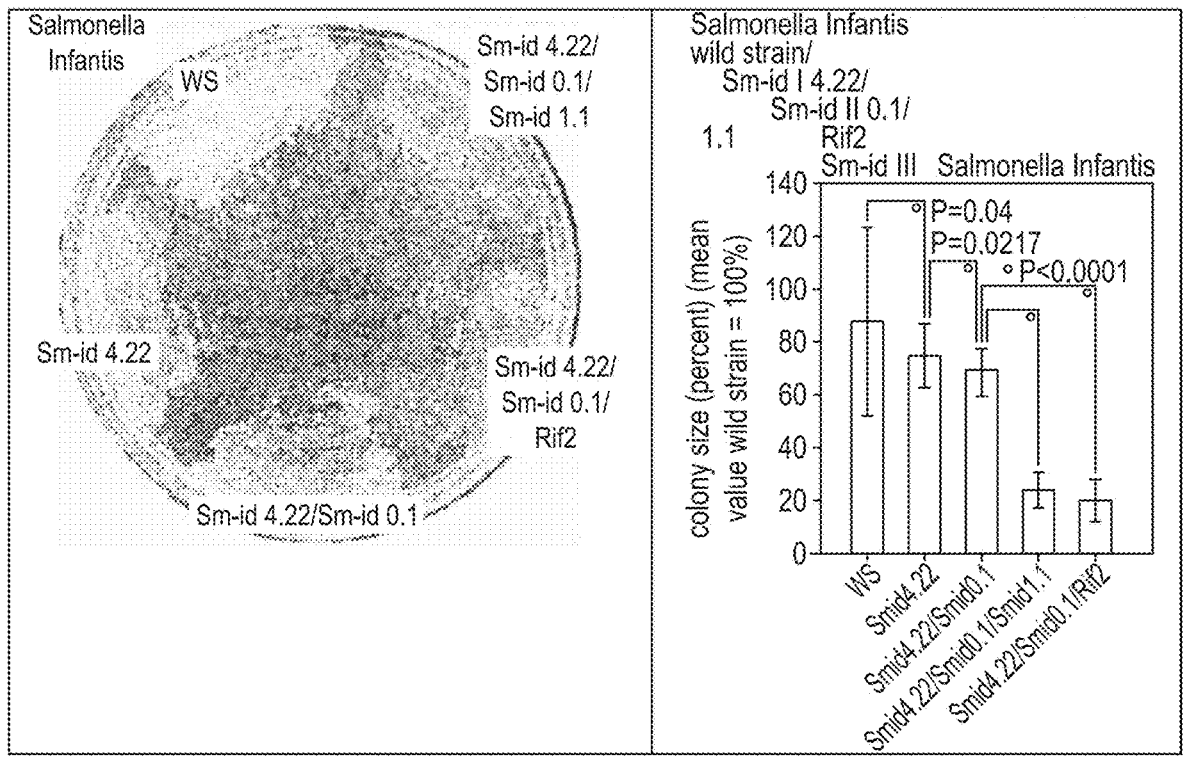

Bjorkman J et al. "Virulence of antibioticresistant Salmonella typhimurium", Proceedings of the National Academy of Sciences, National Academy of Sciences, vol. 95, Jan. 1, 1998 (Jan. 1, 1998), pp. 3949-3953.
Revolledo and Ferreira: "Salmonella antibiotic-mutant strains reduce fecal shedding and organ invasion in broiler chicks", Poultry Science, vol. 89, No. 10, Oct. 1, 2010 (Oct. 1, 2010), pp. 2130-2140.
Linde K et al. "Prophylaxis of Salmonella abortus ovis-induced abortion of sheep by a Salmonella typhimurium live vaccine." Vaccine 1992, vol. 10, No. 5, 1992, pp. 337-340. (Abstract Only).
Linde K et al. "Stable Listeria monocytogenes live vaccine candidate strains with graded attenuation on the mouse model", Vaccine, vol. 9, No. 2, Feb. 1, 1991 (Feb. 1, 1991), pp. 101-105. (Abstract Only).
Linde K et al. "Bacterial live vaccines with graded level of attenuation achieved by antibiotic resistance mutations: transduction experiments on the functional unit of resistance, attenuation and further accompanying markers.", Veterinary Microbiology, May 1998, vol. 62, No. 2, May 1998 (May 1998), pp. 121-134.

* cited by examiner

PREPARATION OF LIVE VACCINES

CROSS REFERENCE TO RELATED APPLICATIONS

The present application is a divisional application of U.S. patent application Ser. No. 14/440,942, filed 6 May 2015, now U.S. Pat. No. 10,828,362, issued 10 Nov. 2020, which is a national phase application pursuant to 35 USC § 371 of International patent application number: PCT/EP2013/068373, filed on 5 Sep. 2013, which claims benefit of priority to European patent application no. 12008206.0, filed on 7 Dec. 2012; all of which are incorporated by reference in their entirety.

DESCRIPTION

The present invention provides a method for the generation of a live vaccine containing stable bacteria carrying at least three attenuating mutations and a vaccine containing bacteria obtained by said method.

Many of the live bacterial vaccines comprise attenuated bacteria that have been manipulated by biomolecular techniques. Unfortunately, most of these vaccines are considered as being insufficient to comply with the requirements of practice for the following reasons:

(a) The production is complex and time consuming, the degree of attenuation cannot be controlled and, accordingly, adaptation to the susceptibility of the host is often unsatisfactory.

(b) Methods of testing (clinical trials) requested by the legislative authority are also elaborate.

(c) The population to be vaccinated is limited.

By contrast, mutants attenuated by metabolic drift (MD) are characterized by the following advantages:

(a) Costs for preparation are low and the degree of attenuation via the desired selection of an increased generation time and, thus, reduced colony size, respectively, is, in principle, almost arbitrary.

(b) When using stable specific vaccine strains having three attenuated MD mutations for vaccination of farm animals, elaborate methods of testing are not required.

(c) Even smaller lot sizes will pay off.

As regards key data of the evolutionary principle of MD attenuation the following should be stressed:

(a) The interplay of pathogenic agent versus host is based on mutual tolerance. Highly susceptible hosts survive as single individuals when accidentally infected by an attenuated mutant of a highly virulent pathogenic agent. The host population rejuvenates via the few surviving individuals. The pathogenic agent proliferates as adapted attenuated strain. Myxomatosis is a typical example of such process. Conclusion: Bacterial populations (as well as populations of fungi and viruses) always contain gradually attenuated mutants, inter alia so-called MD mutants.

(b) MD mutants represent clones having mutations in metabolic compartments per definitionem resulting in dysfunction (i.e. attenuation=fitness cost). As a consequence, gradually reduced colony sizes (depending on the clone) compared to the wild strain can be found. Normally, these mutants are eliminated by the immuno competent host or, alternatively, are overgrown by the adapted normal flora.

(c) The reduced colony sizes of the MD mutants inversely correlate with the (prolonged) generation time and the (increasing) degree of attenuation.

(d) The convincing efficacy of MD attenuated test vaccines and vaccines has been proven.

MD mutants can be selected and isolated as:

(a) spontaneous MD antibiotic resistence (MD "res") clones of, e.g., streptomycin, rifampicin, fosfomycin, fusidic acid, and nalidixic acid. These clones can be isolated with a frequency of more than 1% in relation to the virulent resistant clones. MD "res" and virulent resistant clones result from different mutations. Accordingly, MD "res" and attenuation can be regarded as a functional entity.

(b) Increased environmental stress tolerance (iet) mutants which indirectly accumulate in the "dying off" culture.

(c) streptomycin independent (Sm-id) suppressor mutants derived from streptomycin dependent (Smd) clones. These two marker mutants consist of a broad spectrum of clones characterized by clone specifically graduated reduced colony sizes and increasing degrees of attenuation, respectively, from almost wild type virulence to over-attenuation (mini colonies). Generally, ribosomal mutations increase the normal misreading (mistranslation) more or less and the exclusive suppressor mutation also causes attenuation.

For immunization of, e.g., populations of chicken with live *Salmonella* and *Campylobacter* vaccines the interruption of the chain of infection to human beings and, as a consequence, the reduction of human enteritides is the primary goal. Normally, chicks tolerate facultative pathogenic *Salmonella* (and generally even *Campylobacter*) without showing any clinical symptoms. Thus, the low virulence of these wild strains for chicks requires vaccine strains showing a moderate degree of attenuation ensuring on the one hand immunogenicity for chicks but excluding on the other hand a hazard for human beings.

One criterion of the efficacy of vaccine strains is, e.g., the verifiable reduction of the degree of colonization after challenge. MD attenuated live vaccines expressing all components of the bacteria (e.g., outer membrane proteins) can be regarded as a practice oriented option, even as regards *Campylobacter*.

Thus, it is possible to develop effective vaccines for facultative pathogenic bacteria such as *Salmonella* and *Campylobacter*, provided over-attenuation is avoided by adjusting to a low or moderate degree of attenuation. In other words, the reduction of colony size as attenuation equivalent should not fall below about 25% of the colony size of the wild strain. In addition, this condition sine qua must be in line with the safety requirements of the WHO:

stability due to the presence of two independent attenuating mutations. The reversion rate per marker is about $10^{-8}$. However, there is a need for developing vaccine strains showing even higher stability, i.e., lower reversion rates, but not over-attenuation. Unfortunately, the introduction of additional mutations to increase the safety of a live vaccine usually leads to an excess of attenuation thereby rendering the vaccine less effective.

Thus, the technical problem underlying the present invention is to provide improved live vaccine strains characterized by increased stability.

The solution of said technical problem is achieved by providing the embodiments characterized in the claims, i.e., to provide improved live vaccine strains with an increased stability based on at least three mutations, yet avoiding over-attenuation and allowing for the adjustment of the attenuation to a desired level. In fact, during the experiments leading to the present invention it could be shown that by use of the MD attenuation vaccine strains characterized by three (or even more) independent attenuating mutations can be generated showing increased stability and a degree of attenuation that does not exceed the degree of attenuation of vaccine strains having two MD "res" attenuating mutations.

In the experiments of the present invention streptomycin was used, however the procedures disclosed in the present invention are not restricted to only this antibiotic. The experiments described below are based on the use of so-called Sm-id clones derived from Smd mutants since these "double marker" mutants (comprising clones showing all degrees of attenuation—from wild strain-like colonies to mini colonies) allow for the generation of vaccine strains showing a degree of attenuation corresponding to the degree of attenuation of MD "res" single marker strains. Strains of the present invention (Sm-id/MD "res") show an increased stability of about $10^{-24}$.

Figure 4A:
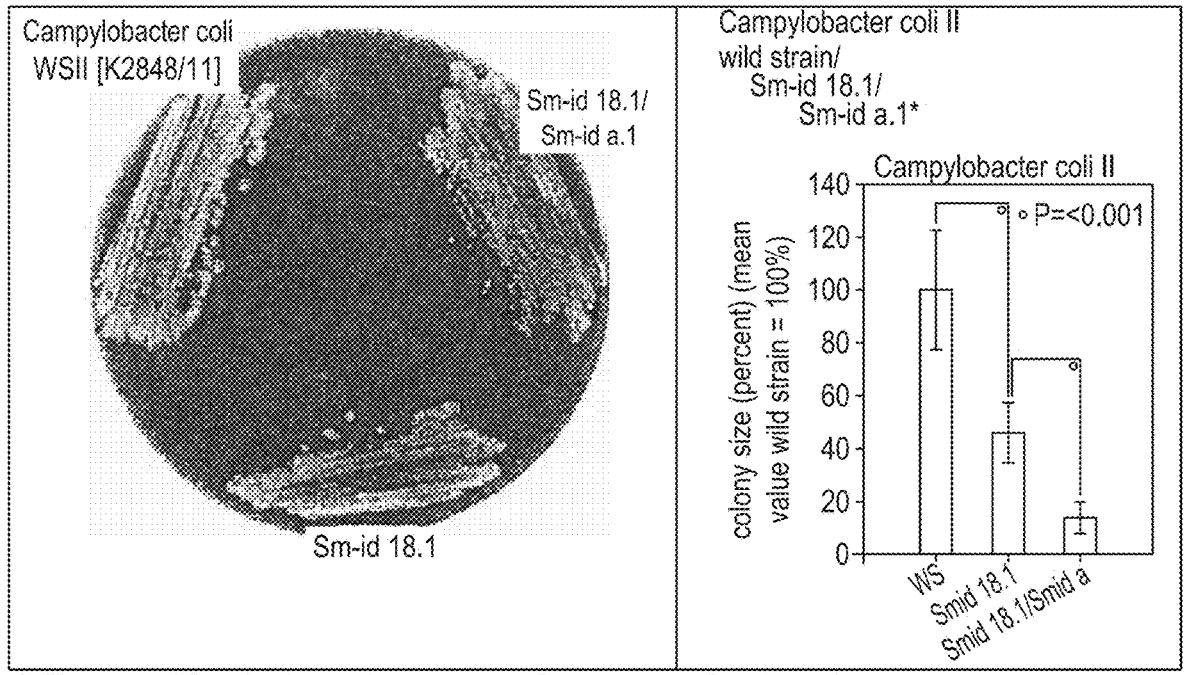

So far, Sm-id/MD "res" vaccine strains of *Salmonella* and *Campylobacter* have not been described in the prior art. In addition, vaccine strains having four, five or even six attenuating mutations generated by the graduated incorporation of two or three Sm-id mutations and an additional MD "res" (A a, A a) marker are novel as well, for streptomycin: Smd 1→Sm-id I→Smd a→Sm-id II→Sm-α→Sm-id III (six attenuating mutations) and Sm-id I/Sm-id II/MD "res" (five attenuating mutations), respectively.

It was found that the particular spectrum of revertants—graduatedly reduced colony sizes—of the Sm-id mutants with combinations of two, four or six markers starts: (a) for Sm-id strains with colony sizes of the wild strain, (b) for Sm-id I/Sm-id II strains with colony sizes of Sm-id I-like colony sizes and (c) for Sm-id I/Sm-id II/Sm-id III constructs the largest colony found only corresponded to Sm-id It Sm-id II-like clones. Thus, these are not wild strain-like revertants.

In principle, the selection and isolation of Smd mutants as starting strains for the generation of Sm-id clones belongs to the state of the art. About 10% of the normal Sm-resistant mutant colonies of, e.g., *Staphyloccoci, Escherichia coli, Bacillus cereus*, are Smd clones (as an apparent biological principle). However, this does not apply to *Salmonella* and *Campylobacter*. The frequency of the appearance of Smd clones of *Salmonella* among the colonies of mutants showing resistance is reported to be about 0.1% or the isolation of such strains is only achievable by use of mutagenesis, respectively.

Interestingly, after analysis of about 5000 Sm resistant mutants the present inventors could not find any Smd strains. In addition, it has to be stressed that the spectrum of Sm-id revertants varies depending on the Smd clone, accordingly, several Smd clones are needed as starting mutants. In other words, the common procedure for selection is inapplicable.

Since presumably ribosomal Smd-pathways are an evolutionary principle of adaptation two possible mechanisms were tested:

(a) Smd-mutants enter the death phase immediately after their formation. Thus, such mutants can only be isolated from log-phase cultures, e.g., from ≤18 h/37° C. cultures but not from ≥48 h/37° C.F cultures (b) During status nascendi the Smd clones are fragile, show delayed growth as mini colonies (which might be overlooked). These mini colonies adapt to "normal growth" during passaging.

For *Campylobacter* there are no data available as regards Smd- and Sm-id mutants. In the literature, there are only some hints as regards Sm-resistant mutants: clones showing high resistance could only be obtained by use of multiple passages against increasing concentrations of streptomycin. A one-step Sm-resistance could only be achieved by use of a concentration of 20 μg streptomycin/ml. Experiments of the present inventors for isolating mutants showing Sm-resistance and Smd-mutants using 100 μg streptomycin/ml (by plating of 72 h/39° C. cultures) failed. Surprisingly, it was found that despite significantly increasing amounts of bacteria the viable counts significantly decreased from the 24 h/39° C. to the 72 h/39° C. culture as shown in the following table.

TABLE 1

*Campylobacter coli* and *Campylobacter jejuni*: Viable counts on Petri dishes with Caso-agar against the incubation period at 39° C.

| Campylobacter | 24 h | 48 h | 72 h |
|---|---|---|---|
| *C. coil* | $1 \times 10^{10}$ | $3 \times 10^{9}$ | $7 \times 10^{8}$ |
| *C. jejuni* | $3 \times 10^{10}$ | $5 \times 10^{9}$ | $1 \times 10^{9}$ |
| *C. coli* Smd | $3 \times 10^{9}$ | $3 \times 10^{8}$ | $4 \times 10^{7}$ |

These results are in line with the observation that cultures of *Campylobacter* are capable of passing into a viable but not culturable status.

Accordingly, mutants having Sm resistance could only be obtained by plating of ≤24 h/39° C. culture material. However, no Smd mutants could be found among the resistant colonies having normal size or slightly reduced size. But among the very small colonies and mini colonies of *Campylobacter* (appearing with distinct delay) the majority of the clones could be characterized as being Smd clones.

BRIEF DESCRIPTION OF THE DRAWINGS

FIGS. 1A-1D show examples of *Salmonella* vaccine strains characterized by three attenuating mutations.

Incubation of the plates was at 37° C. for about 20 hours and resulted in the following:

FIG. 1A *Salmonella Infantis* (wild strain/Sm-id 4.22/Rif 2 (and Iet 4));

FIG. 1B *Salmonella Virchow* (wild strain/Sm-id 9.3/Rif 2);

FIG. 1C *Salmonella Hadar* (wild strain/Sm-id 4.1/Sm 2 (and Rif 1);

FIG. 1D *Salmonella Paratyphi* B, variant Java 3.2 (wild strain/Sm-id.1.1/Rif 3 (and Rif 2)).

FIGS. 2A-2D show examples of *Campylobacter* vaccine strains characterized by three attenuating mutations Incubation of the plates was at 39° C. for about 48 and 72 hours, respectively and resulted in the following:

FIG. 2A *Campylobacter coli* I (wild strain/Sm-id 5.5/Pho 1 and Pho 2);

FIG. 2B *Campylobacter coli* II (wild strain/Sm-id 18.1/Sm 2);

FIG. 2C *Campylobacter jejuni* I (wild strain/Sm-id 2.3/Pho 1 (and Pho 2));

FIG. 2D *Campylobacter jejuni* II (wild strain/Sm-id 2.1/Sm 2).

FIGS. 3A-3B show examples of *Salmonella* vaccine constructs characterized by (two), four, five or six attenuating mutations. Incubation of the plates was at 37° C. for about 20 hours and resulted in the following:

FIG. 3A *Salmonella Virchow:* wild strain/Sm-id I 1.4/Sm-id II 0.3/Sm 4;

wild strain/Sm-id I 1.4/Sm-id II 0.3/Sm-id III 0.x.

FIG. 3B *Salmonella Infantis:* wild strain/Sm-id I 4.22/Sm-id II 0.1/Rif 2;

wild strain/Sm-id I 4.22/Sm-id II 0.1/Sm-id III 1.1.

FIGS. 4A-4B show examples of *Campylobacter* vaccine constructs characterized by (two), four, five or six attenuating mutations. Incubation of the plates was at 39° C. for about 48 hours and resulted in the following:

FIG. 4A *Campylobacter coli* II wild strain/Sm-id I 18.1/ Sm-id II a.1. This strain is characterized in that the second Sm-id a.1 mutation results in an Sm resistance.

Figure 4B:
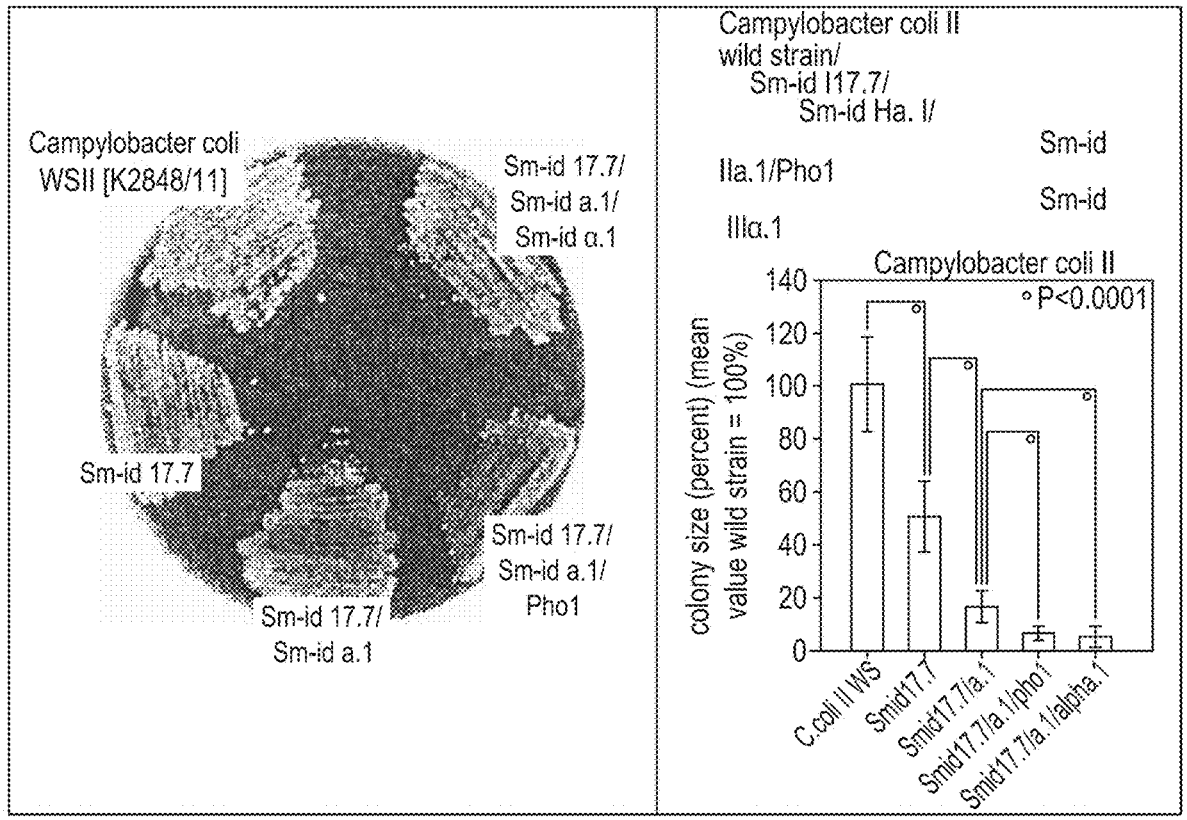

FIG. 4B *Campylobacter coli* II wild strain/Sm-id I 17.7/ Sm-id II a.1/Phol, wild strain/Sm-id I 17.7/Sm-id II a.1/Sm-id III a.1.

Thus, the present invention provides a method for the generation of a bacterial live vaccine containing stable bacteria carrying at least three (and up to six or seven) attenuating mutations, wherein said method comprises the following steps:

(a) providing a bacterial strain and growing said strain in the presence of a first antibiotic, preferably streptomycin;

(b) isolating from the strain of (a) such "mini" colonies which correspond to clones which are dependent on the first antibiotic;

(c) growing a clone of (b) in the absence of the first antibiotic and isolating attenuated revertants characterized by a colony size which is ≥50% of the colony size of the wild strain;

(d) growing a clone obtained in step (c) in a medium supplemented with a second antibiotic that may differ from the first antibiotic (e.g., an aminoglycoside such as streptomycin, neomycin, kanamycin, spectinomycin, gentamicin, amikacin, and tobramycin; rifampicin, fusidic acid, nalidixic acid, fosfomycin,) having a suitable concentration, preferably an about tenfold MIC;

(e) isolating and serially passaging colonies showing reduced size (MD A "res"); and (f) isolating clones having the graduated reduction of the colony size as stable property.

The bacterial strain of step (a) is, preferably, obtained from "wild" virulent strains. These strains can be taken from diseased animals (e.g., chicken). The starting natural strains which are used should have a certain degree of virulence.

The choice of the antibiotic for selecting the mutants of step (a) is guided by reasons of a practical nature. For example, streptomycin is known to lead rapidly to the development of resistant and dependent strains among the micro-organisms.

Thus, in a preferred embodiment of the method of the present invention the antibiotic of step (a) is streptomycin. However, other aminoglycoside antibiotics such as neomycin, kanamycin, spectinomycin, gentamicin, amikacin, and tobramycin, and rifampicin, fusidic acid and nalidixic acid may also be suitable as the antibiotic of step (a).

It is known that resistance to the antibiotic can result from different modification mechanisms. In particular, the genetic modification may affect a chromosome of the bacterium. The chromosomal modification is a rare event which, once carried out, ensures the stability of the acquired properties.

The term "mini colonies" as used herein relates to bacterial colonies characterized by a reduction of size. Preferably, they are characterized by a size of ≤10% of the corresponding wild strain colonies.

The selection of attenuated bacterial strains as a function of growth criteria on media containing an antibiotic is an operation which has been used for various species with the object, notably, of causing the appearance of strains having reduced virulence.

The bacterial strains according to the invention characterized by at least three (and up to six or seven) attenuating mutations are in the first place non-virulent strains selected, from natural virulent strains, for their growth capacity on a medium with a high content of an antibiotic such as streptomycin, and in addition, which can only be developed satisfactorily in the presence of the antibiotic (step (b). For this reason, these strains are said to be dependent on, e.g., streptomycin (Smd mutant).

In the second place, the strains of step (c) are mutants selected from the antibiotic dependent strains and which have the particularity of being able to develop in the absence of streptomycin due to the introduction of a second attenuating mutation or marker. These strains are called Sm-id strains. Preferably, a washing step is carried out between steps (b) and (c). The preferred medium for step (c) is a *Salmonella* Caso (SC) medium (e.g., for *Salmonella*) or a Caso medium (e.g., for *Campylobacter*).

Step (d) allows introducing an additional MD antibiotic resistance ("res") mutation (as a third attenuating marker). Preferably, the antibiotic is streptomycin, rifampicin or fosfomycin. The concentration of the antibiotic in step (d) can be determined by the person skilled in the art according to routine procedures. Preferably, for *Salmonella* the concentration of rifampicin, streptomycin (note: most Sm-id mutants are streptomycin sensitive and therefore suited for an additional MD Sm "res" marker) and fosfomycin corresponds to an MIC value of about tenfold, and for fusidic acid to an MIC value of about fourfold. Preferably, for *Campylobacter*, at least 200 μg fosfomycin/ml and at least 100 μg streptomycin/ml, respectively, are used.

In step (e) the Sm-id/MD antibiotic "res" strains of the previous step characterized by an additional reduced slight colony size are isolated and serially passaged in order to check stability. Preferably, at least 30 serial passages are carried out.

Finally, in step (f) the clones isolated from step (e) having the graduated reduction of the colony size as stable property are provided.

In a preferred embodiment of the method of the invention steps (a) to (c) are at least repeated once for the generation of bacteria carrying at least four attenuating mutations. This method allows to generate new attenuating mutants, e.g., according to the following schemes (shown for Sm):

(a) Smd 1→Sm-id I→Smd a→Sm-id II;

(b) Smd 1→Sm-id I→Smd a→Sm-id II→Smd α→Sm-id III;

(c) Smd 1→Sm-id I→Smd a→Sm-id II→Smd α→Sm-id III→MD antibiotic "res".

Surprisingly, it was found that strains derived from Sm-id mutants carrying four or even six mutations do not show a higher degree of attenuation, compared to the strains having three attenuating mutations, but an even higher stability.

The choice of the antibiotic for selecting the MD antibiotic "res" mutant strains according to the present invention is guided by reasons of a practical nature and, in principle, any antibiotic capable of inducing metabolic drift (MD) mutations can be used for the purposes of the present invention, e.g., streptomycin (note: most Sm-id mutants are streptomycin sensitive and therefore suited for an additional MD Sm "res" marker), rifampicin, fosfomycin, fusidic acid or nalidixic acid.

The method of the present invention is not restricted to particular bacteria. Besides *Salmonella* sp. and *Campylobacter* sp., other bacteria such as *Staphylococcus aureus, Escherichia coli, Bacillus cereus* (Pseudoanthrax), *Yersinia* sp. such as *Y. pestis, Klebsiella* sp., *Listeria* sp., *Aeromonas* sp., *Shigella* sp., *Pasteurella/Avibacterium* sp., *Riemerell* a sp., *Ornithobacterium rhinotracheale, Bordetella* sp., and *Pseudomonas* sp. can also be used for generating bacterial live vaccine containing stable bacteria according to the methods of the present invention.

However, preferred bacteria are *Salmonella* and/or *Campylobacter*, especially *Salmonella bongori*, the *S. enterica* subspecies *enterica, arizonae, diarizonae, salamae, houtenae* and *indica*, preferably *S. enterica* subspecies *enterica* such as the following Serovars: Dublin, *gallinarum* (biovars *gallinarum* and *pullorum*), *Choleraesuis*, Typhisuis, Typhi, Paratyphi A,B,C, Abortusequi, Abortusovis, Abony, Enteritidis, Typhimurium, Copenhagen, *Infantis, Virchow, Hadar, Agona*, Newport, *Anatum*, Heidelberg, Panama, Indiana, Saintpaul, Brandenburg, and *Campylobacter coli, Campylobacter jejuni*, and *Campylobacter fetus*.

In a preferred embodiment of the method of the present invention in steps (a) and (b) *Salmonella* mutants are isolated from log phase cultures and as mini-colonies that start appearing after at least or more than 48 h at 37° C. incubation.

In a further preferred embodiment of the method of the present invention in steps (a) and (b) *Campylobacter* mutants are isolated as mini-colonies that start appearing after at least or more than 72 h at 39° C. incubation.

The present invention also provides alive bacterial strains obtainable by the method of the invention as well as a vaccine comprising alive bacterial strains of the invention and a biologically acceptable carrier. The vaccinating compositions may of course be constituted by means of freshly cultivated bacteria.

Preferably, the vaccine composition of the present invention is freeze-dried.

To administer the vaccinating bacteria, the medium in which they are suspended is not critical. Of course, this medium must not interfere with the good viability of the bacteria that they contain.

The vaccine of the present invention is administered in an amount suitable for immunization of an individual and may additionally contain one or more common auxiliary agents. The employed term "amount suitable for immunization of an individual" comprises any amount of bacteria with which an individual can be immunized. An "amount suitable for immunization of an individual" may be determined using methods known to one skilled in the art. The term "individual" as used herein comprises an individual of any kind. Examples of such individuals are animals (and humans).

The administration of the vaccine preferable is the oral route but also injection may be made at various sites of the individual intramuscularly, subcutaneously, intradermally or in any other form of application. It may also be favourable to carry out one or more "booster injections" having about equal amounts.

The vaccine of the present invention may be prophylactic, that is, the compounds are administered to prevent or delay the development of an infection or colonisation, e.g. an infection/colonisation caused by *Salmonella* or *Campylobacter*.

The following strains have been deposited with the German Type Culture Collection (Deutsche Sammlung von Mikrorganismen and Zellkulturen (DSMZ), Braunschweig) on Nov. 27, 2012 under the Budapest Treaty:

| Name | Accession Number |
| --- | --- |
| *Salmonella enterica* ssp. *enterica* Serovar *Infantis* Smid4-22/Rif2 = | DSM 26682 |
| *Campylobacter coli* K2848/11 Smid18/Sm2 = | DSM 26683 |
| *Campylobacter jejuni* K2963/12 Smid2.1/Sm2 = | DSM 26684 |

The below examples explain the invention in more detail.

Example 1

Materials (A) Strains

*Salmonella enterica* subsp. *enterica* serovar *Virchow*,
*Salmonella enterica* subsp. *enterica* serovar *Infantis*,
*Salmonella enterica* subsp. *enterica* serovar *Hadar*,
*Salmonella paratyphi* B (var. L-Tartrat+, formerly Java),
*Campylobacter coli, Campylobacter jejuni* (provided by Lohmann Animal Health, Cuxhaven, Germany).

(B) Media 1000 ml *Campylobacter* medium (Caso-medium) contain: 35 g Caso Agar (Sifin), 3 g yeast extract, 3 g casein hydrolysate, 4 g activated carbon, 0.25 g $FeSO_4$, 0.25 g sodium pyruvate, 5 g agar Kobe (Roth).

1000 ml *Salmonella* medium (SC-medium) contain: 35 g Caso Agar (Sifin), 3 g yeast extract, 1 g glucose, 5 g agar Kobe (Roth).

(C) Antibiotics

Streptomycin (Sm) (Roth No. 0236.2), fosfomycin (Pho) (Sigma No. P5396), rifampicin (Rif) (Riemser Arzneimittel AG, Fatol Eremfat 600 mg)

(D) MIC Values of Wild Type Strains

| Strain | Streptomycin | rifampicin | fosfomycin |
| --- | --- | --- | --- |
| *Salmonella enterica* subsp. *enterica* serovar *Virchow* | 12.5 | 12.5 | n.d. |
| *Salmonella enterica* subsp. *enterica* serovar *Infantis* | 12.5 | 12.5 | n.d. |
| *Salmonella enterica* subsp. *enterica* serovar *Hadar* | 25 | 12.5 | n.d. |
| *Salmonella paratyphi* B (var. L-tartrate+) | 30 | 12.5 | n.d. |
| *Campylobacter coli* WS I | 1 | n.d. | 25 |
| *Campylobacter coli* WS II | 1 | n.d. | 25 |
| *Campylobacter jejuni* WS I | 2 | n.d. | 25 |
| *Campylobacter jejuni* WS II | 2 | n.d. | 25 | n.d.: not determined

Example 2

Selection and Isolation, of Smd Mutants (a) Practice-Orientated Isolation of Smd Mutants of *Salmonella*

About $10^{10}$ cfu of a 18 h/37° C. culture of *Salmonella* were plated on a Petri dish containing SC agar supplemented with 500 μg streptomycin/ml. Besides colonies having normal sizes and single colonies having slightly decreased sizes (virulent Sm resistant clones and MD Sm "res" clones) "mini colonies" (predominantly small colony variants=scv) with varying frequencies—depending on the strain—could be detected. After an incubation time of about ≥48 h (at 37° C.) 1 to 2 additional mini colonies (per about 30 colonies having normal sizes and colonies having slightly decreased sizes) could be detected that could not be distinguished from scv. Depending on the frequency of appearance of the scv phenotype 3% to 20% of these mini colonies could be shown to represent Smd mutants.

The calculated frequency of the Smd clones in relation to resistant mutants was ≥1%.

Note: The isolation of Smd clones is achieved by use of Sm sensitive wild type strains as the starting material. Strains preferably have a low MIC value.

(b) Practice-Orientated Isolation of Smd Mutants of *Campylobacter*

Bacterial material obtained from a Caso agar Petri dish culture (24 h/39° C.; about $10^{10}$ cfu) that had been inoculated in such a way that the entire surface of the disc was covered was plated on 1 or 2 Caso agar Petri dishes supplemented with 100 μg streptomycin/ml and incubated for 72 h at 39° C. Depending on the strain ≤10 colonies/plate (average value) having normal sizes and colonies having slightly decreased sizes (streptomycin resistant and MD Sm "res" clones) were detectable. In addition, colonies having a clearly reduced size (diameter is ≤25% of the normal size) with a frequency of about 20%—compared to the colonies having normal sizes and colonies having slightly reduced sizes—could be detected. About one-third of these colonies were Smd clones.

The calculated frequency of the Smd clones in relation to resistant mutants was ≥5%.

Example 3

Selection and Isolation of Sm-Id Mutants (a) Isolation of *Salmonella* Sm-Id Mutants from Smd Clones About $10^9$ cfu (per petri dish) of a washed Smd mutant were plated with SC medium and incubated for 48 h at 37° C. From the attenuated revertants obtained only such mutants were further treated that showed a colony size of about 50% compared to the wild type strain colonies (according to the objective to obtain Sm-id clones having only low attenuation).

(b) Isolation of *Campylobacter* Sm-Id Mutants from Smd Clones

Bacterial material obtained from a Caso agar (supplemented with 100 μg streptomycin/ml) Petri dish culture (24 h/39° C.) that had been inoculated in such a way that the entire surface of the disc was covered was subjected to one washing step, plated on Caso medium in a ratio of 1:1 (about $3 \times 10^9$ cfu) to 1:4 and then incubated for 72 h at 39° C. Under these culturing conditions the majority of Smd clones showed the development of ≤10 attenuated revertants (on average). Most of these attenuated revertants were Sm sensitive. Generally, Sm-id clones showing a reduced colony size of about ≥50% compared to the wild type strain colonies were further processed.

Some strains, e.g., *Campylobacter jejuni*, allowed isolation only from Sm-id having a colony size of ≤50% compared to the wild type strain.

Note: Not all *Campylobacter* strains and the Smd mutants derived thereof allow isolation of Sm-id revertants without any problems. However, it is possible to isolate Sm-id revertants also from the problematic strains using, for example, several independent Smd mutants.

Example 4

Isolation of an Additional MD Antibiotic "Res" Mutant

The incorporation of an additional MD antibiotic "res" mutation in selected Sm-id mutants as third marker for attenuation and recognition was carried out as already described above.
Briefly, (a) *Salmonella:* $10^{9-10}$ cfu of the selected Sm-id clones were incubated on SC medium supplemented with an about tenfold MIC value concentration of rifampicin or streptomycin (as regards fusidine acid the about fourfold MIC value concentration), respectively, and incubated for 48 hours at 37° C.

(b) *Campylobacter*: The material of a Petri dish culture (Caso medium) that was inoculated with the Sm-id mutant in such a way that it covered the whole surface and incubated for 24 h at 39° C. was plated at a ratio of 1:4 to 1:8 on Caso medium supplemented with 200 μg fosomycin/ml or 100 μg streptomycin/ml and incubated for ≥72 h at 39° C.

The colonies showing (more or less) reduced sizes were isolated and subjected to serial passages. About 20% of these clones maintained the clone specifically graded reduction of colony size as a stabile feature.

Example 5

Generation of Vaccine Strains Having 4 or 6 Attenuated Mutations

The generation of vaccine strains having 4 or 6 attenuated mutations was achieved by sequentially incorporating a second and, optionally, a third Sm-id suppressor mutation into a basic Sm-id I clone: Sm-id I/Sm-id II/Sm-id III.

(a) *Salmonella*: About $10^{10}$ cfu of the basic Sm-id I mutant (or the Sm-id II starting strain) were plated on SC medium supplemented with 500 μg streptomycin/ml and incubated for 48 h at 37° C. About 5% of Sm-resistant colonies are Smd mutants (now growing primarily as colonies having "normal sizes"). By use of these Smd clones derived from Sm-id I strains and Sm-id II strains, respectively, Sm-id mutants were again isolated according to the approach described in Example 3a. Clones having the desired reduction of colony size were treated further.

(b) *Campylobacter*: The material obtained from a Caso medium Petri dish culture that was inoculated with an Sm-id mutant in such a way that the entire surface was covered and incubated for 24 h at 39° C. was plated at a ratio of 1:4 on Caso medium supplemented with 100 μg streptomycin/ml and incubated for 72 h at 39° C. Besides the about 15 Sm resistant colonies having a "normal size" 2 to 3 small colonies could be detected. 50% of these colonies are Smd clones. These Smd clones (derived from Sm-id I strains and Sm-id II strains, respectively) were used as starting clones—according to Example 3(b)—for again isolating Sm-id mutants. Clones showing the desired reduction of colony size were treated further.

Example 6

Isolation of an MD Antibiotic "Res" Mutant from Selected Sm-Id II Mutants (a) *Salmonella*: The incorporation of an advantageous MD antibiotic "res" mutation into selected Sm-id I/Sm-id II mutants as an additional $5^{th}$ attenuation—and recognition marker was carried out analogously according to the approach described in Example 4(a).

(b) *Campylobacter*: The incorporation of an advantageous MD antibiotic "res" mutation into selected Sm-id I/Sm-id II mutants as an additional $5^{th}$ attenuation- and recognition marker was carried oat analogously according to the approach described in Example 4(b).

Note: The approach described above can also be used for the additional incorporation of an MD antibiotic "res" mutation into selected Sm-id III mutants (having six attenuated mutations) as $7^{th}$ marker for attenuation and recognition. However, this might result in over-attenuation, which might interfere with relevancy to practice.

Example 7

Colony Sizes Converted to Bar Graphs for Prospectively Oriented Evaluation of the Probable Degree of Attenuation Suspensions of the corresponding wild type strains and the MD mutants derived from these strains are diluted logarithmically and then plated on culture medium in such a way that per Petri dish 10 to 50 well definable single colonies can be obtained. At least 5 Petri dishes per grade of dilution are prepared in order to compensate for differences in growth due to the medium. Single colonies grown under standardized conditions (e.g., identical times of incubation, identical layer thicknesses of the medium) are photographed. Digital photographs are processed with the Cell-Profiler program (Broad Institute): The diameters of the individual colonies were determined and saved. After averaging of the values the data are plotted as bar graphs in relation to the sizes of the wild type strain colonies (given as 100%).

Example 8

Preparation of Vaccines from Suitable Vaccine Strains and Use for Vaccination of Chicks/Chicken and Further Hosts to be Protected, Respectively For the preparation of live vaccines vaccine strains harbouring three (four, five and six, respectively) attenuating mutations were grown in common liquid media up to logarithmic phase. Vaccine suspensions and vaccine sediments, respectively, were supplemented with a suitable stabilisator and subsequently lyophilized. The vaccines obtained were administrated (according to the kind of indication one, two or three doses) by oral or parenteral administration.

The invention claimed is:

1. A method of generating a stable attenuated bacterial strain carrying three to seven attenuating metabolic drift (MD) mutations, wherein said method comprises the steps of:
   (a) obtaining a starting natural bacterial strain and growing said strain in the presence of a first antibiotic to obtain a mini colony of the strain bearing the first attenuating MD mutation;
   (b) isolating colonies of the strain obtained in step (a) that are dependent on the first antibiotic, wherein the colonies have a mini colony size of ≤10% as compared to colonies of a corresponding starting natural bacterial strain;
   (c) growing a colony of the strain obtained in step (b) in the absence of the first antibiotic and isolating attenuated colonies characterized by a colony size of ≥50% as compared to colonies of the corresponding starting natural bacterial strain;
   (d) growing a colony of the strain obtained in step (c) in a culture medium supplemented with a second antibiotic;
   (e) isolating and serially passaging colonies of the strain obtained in step (d) to identify colonies stably being of greater than 25% in size as compared to colonies of the corresponding starting natural bacterial strain; and
   (f) isolating colonies of the strain obtained in step (e) having said size of greater than 25% as the stable attenuated bacterial strain,
   wherein the first antibiotic is selected from the group consisting of streptomycin, neomycin, kanamycin, spectinomycin, gentamicin, amikacin, tobramycin, rifampicin, fusidic acid, and nalidixic acid;
   wherein the second antibiotic is selected from the group consisting of streptomycin, neomycin, kanamycin, spectinomycin, gentamicin, amikacin, tobramycin, rifampicin, fusidic acid, nalidixic acid, and fosfomycin;
   to provide the stable attenuated bacterial strain carrying said three to seven attenuating MD mutations
   wherein the bacterial strain is selected from the group consisting of *Aeromonas* species (sp.), *Bacillus cereus*, *Bordetella* sp., *Campylobacter* species (sp.), *Escherichia coli*, *Klebsiella* sp., *Listeria* sp., *Ornithobacterium rhinotracheale*, *Pseudomonas* sp., *Riemerella* sp., *Pasteurella/Avibacterium* sp., *Salmonella* sp., *Shigella* sp., *S taphylococcus aureus*, and *Yersinia* sp.;
   wherein a colony of the attenuated bacterial strain having the mini colony size of ≤10% as compared to a colony of the corresponding starting natural bacterial strain defines a mini colony;
   wherein the colony size is determined by the diameter of the colony; and
   wherein the stable attenuated bacterial strain carrying said three to seven attenuating MD mutations is not over-attenuated.

2. The method of claim 1, wherein the stable attenuated bacterial strain is *Salmonella* or *Campylobacter*.

3. The method of claim 1, wherein the first antibiotic is streptomycin and the second antibiotic is rifampicin.

4. The method of claim 2, wherein the *Salmonella* strain having the mini colony size of ≤10% in step (b) and the *Salmonella* strain having the colony size of ≥50% in step (c) are isolated from cultures as the mini colonies that start appearing after at least or more than 48 hours of incubation at 37°C.

5. The method of claim 1, wherein the *Campylobacter* strain grown in the presence of the first antibiotic in step (a) and isolated in step (b) are isolated as the mini colonies that start appearing after at least or more than 72 hours of incubation at 37° C.

6. The method of claim 1, wherein the bacterial strain carries at least four attenuating MD mutations, and steps (a) to (c) are repeated at least once.

7. The method of claim 1, wherein at least 30 serial passages are carried out in step (e).

8. The method of claim 1, wherein the second antibiotic in step (d) is in fourfold and up to tenfold MIC concentration.

9. The method of claim 1, wherein the second antibiotic is rifampicin, streptomycin, or fosfomycin, which is at a tenfold MIC concentration.

10. The method of claim 1, wherein the second antibiotic is fusidic acid, which is at a fourfold MIC concentration.

11. The method of claim 1, wherein the bacterial strain is *Salmonella*, the first antibiotic is streptomycin, and the second antibiotic is rifampicin .

* * * * *